United States Patent [19]

Paradis

[11] Patent Number: 4,507,120
[45] Date of Patent: Mar. 26, 1985

[54] SUCTION CANISTER WITH CORRUGATED ADJUSTABLE SUCTION INLET

[76] Inventor: Joseph R. Paradis, 60 Plymouth Rd., Holden, Mass. 01520

[21] Appl. No.: 370,562

[22] Filed: Apr. 21, 1982

[51] Int. Cl.³ .............................................. A61M 1/00
[52] U.S. Cl. .................................... 604/320; 141/59; 137/205
[58] Field of Search ............................... 604/317–321; 128/760, 766, 771; 137/205, 577, 393, 453, 123, 152; 55/158, 164, 387, 511, 501, 503; 141/7, 8, 59, 65, 21, 40, 42, 43, 192, 198, 374

[56] References Cited

U.S. PATENT DOCUMENTS

| | | | |
|---|---|---|---|
| 2,665,706 | 1/1954 | Hanson | 137/393 |
| 3,002,870 | 10/1961 | Belgrade et al. | 55/503 |
| 3,782,083 | 1/1974 | Rosenberg | 55/501 |
| 4,111,204 | 9/1978 | Hessel | 604/320 |
| 4,186,782 | 2/1980 | Scharf | 141/7 |
| 4,203,462 | 5/1980 | Beller | 137/393 |

OTHER PUBLICATIONS

ITHAT Cat. Cut., Medi-Vac. Corp., Abilene, Texas, 79604, 1979.
Gove-Tex Membrane Product Catalog Cut, W. L. Gore & Assoc., Elkton, Md., 1980.

Primary Examiner—C. Fred Rosenbaum
Assistant Examiner—J. L. Kruter
Attorney, Agent, or Firm—George E. Kersey

[57] ABSTRACT

Apparatus for the collection of fluids, particularly body fluids in a disposable container with a removable lid to which suction is applied. In order to avoid contamination of the suctional system from the fluids being collected, a removable filter chamber, with a hydrophobic filter element, is interposed in a suctional tube that extends downwardly from the lid to the cut-off level of the fluid in the container. When the fluid collected in the container rises to the cut-off level, it is sucked against the filter and the outlet is sealed.

9 Claims, 6 Drawing Figures

SUCTION CANISTER WITH CORRUGATED ADJUSTABLE SUCTION INLET

BACKGROUND OF THE INVENTION

This invention relates to the collection of fluids, and, more particularly, to the collection of body fluids using suction collection equipment.

In many medical and other procedures it is necessary to collect fluids that form, for example, in the body of a patient, often as a result of operating procedures or in connection with diseases which produce undesired fluids in various body cavities, such as the lungs. More frequently, the fluid is in the form of blood which is suctioned and aspirated during cleaning procedures. In these cases there is a danger from contact with the collected fluids.

Thus, when material is aspirated from the respiratory tract there is a serious risk of having health care workers acquire herpes virus from patients with occult infections. Similarly, the personnel of operating rooms have a serious risk of acquiring hepatitis B from contact with blood of HB Ag-positive patients. In addition, many surgical procedures are associated with infections where implants or high-flow suction is used. In coronary bypass procedures suction lines are used to return aspirated blood from a wound to an oxygenator. Thereafter the blood is returned to the patient. When the line is not aspirating blood, it is aspirating room air which mixes with the blood in the machine and increases the risk of patient infection.

Moreover, the suctional process creates a froth or a foam of the fluid being collected. This gives rise to mists and aerosols which can spread through the collection system and produce infections unless special precautions are taken.

Numerous attempts have been made to devise disposable containers for use with suctional equipment with special valving to reduce the danger from the undesired spread of infection-laden aerosols and mists throughout the collection system. Representative collection techniques are illustrated in the following patents:

| U.S. Pat. No. | Issued | Inventor |
| --- | --- | --- |
| 3,685,517 | 8/22/72 | G. S. Reynolds, et al. |
| 3,699,315 | 10/24/74 | L. K. Holbrook |
| 3,811,485 | 5/21/74 | L. K. Holbrook |
| 3,863,663 | 2/4/75 | W. J. Bornhorst |
| 3,965,902 | 6/29/76 | R. J. Reilly et al. |
| 4,245,637 | 1/20/81 | R. L. Nichols |

While providing improved and safer performance, the usual valving arrangements are complex, costly and insufficiently reliable. They often result in termination of the suction before the cannister is appropriately filled. In some cases the avoidance of system contamination requires that the closure valve be operated when the collection container is less than half, and sometimes only one-third, full. This is often the result of early operation of the valve because of the froth generated during the collection process. In such a case, if an attempt is made to restart the equipment after an initial valve closure, there is a serious danger of system contamination. In other cases even when the buildup of froth is not serious, the aerosol particles that are created during suction are able to pass through the valving into the collection line.

Accordingly, it is an object of the invention to facilitate the collection of fluids. A related object is to facilitate the collection of body fluids. Another related object is to facilitate the collection of body fluids using suctional equipment.

Still another object of the invention is to simplify the control over suction used in the collection of fluids. A related object is to achieve suitable control over suction without using any valving arrangement.

Yet another object of the invention is to enhance the efficiency with which collection can be made of body fluids. A related object is to achieve efficient collection of body fluids while reducing the danger of contamination to the collection system.

SUMMARY OF THE INVENTION

In accomplishing the foregoing and related objects, the invention provides a filter chamber interposed in a suctional inlet suspended from the removable closure of a collection container. The closure includes an inlet port for fluids being collected and an outlet port near the center of the container. The filter chamber contains a semi-permeable filter element which desirably is hydrophobic. When the level of collected fluid reaches the opening of the suctional inlet, the fluid is drawn into the chamber against the semi-permeable element to block the suctional effect and terminate the filling operation.

In accordance with one aspect of the invention, the suctional inlet and the filter chamber are removable from the closure, This permits a series of the collection containers to be connected in series, with only the last container having the control filter.

In accordance with another aspect of the invention, the suctional inlet is positionable at different cut-off levels. The filter chamber, advantageously, is bounded by fins which extend radially from a circular outlet to support the filter element. The filter chamber desirably has a fluid collection compartment with a polished knife edge which is engaged by the filter element to enhance the seal with respect to the outlet.

DESCRIPTION OF THE DRAWINGS

Other aspects of the invention will become apparent after considering several illustrative embodiments taken in conjunction with the drawings, in which.

DETAILED DESCRIPTION

Figure 1:
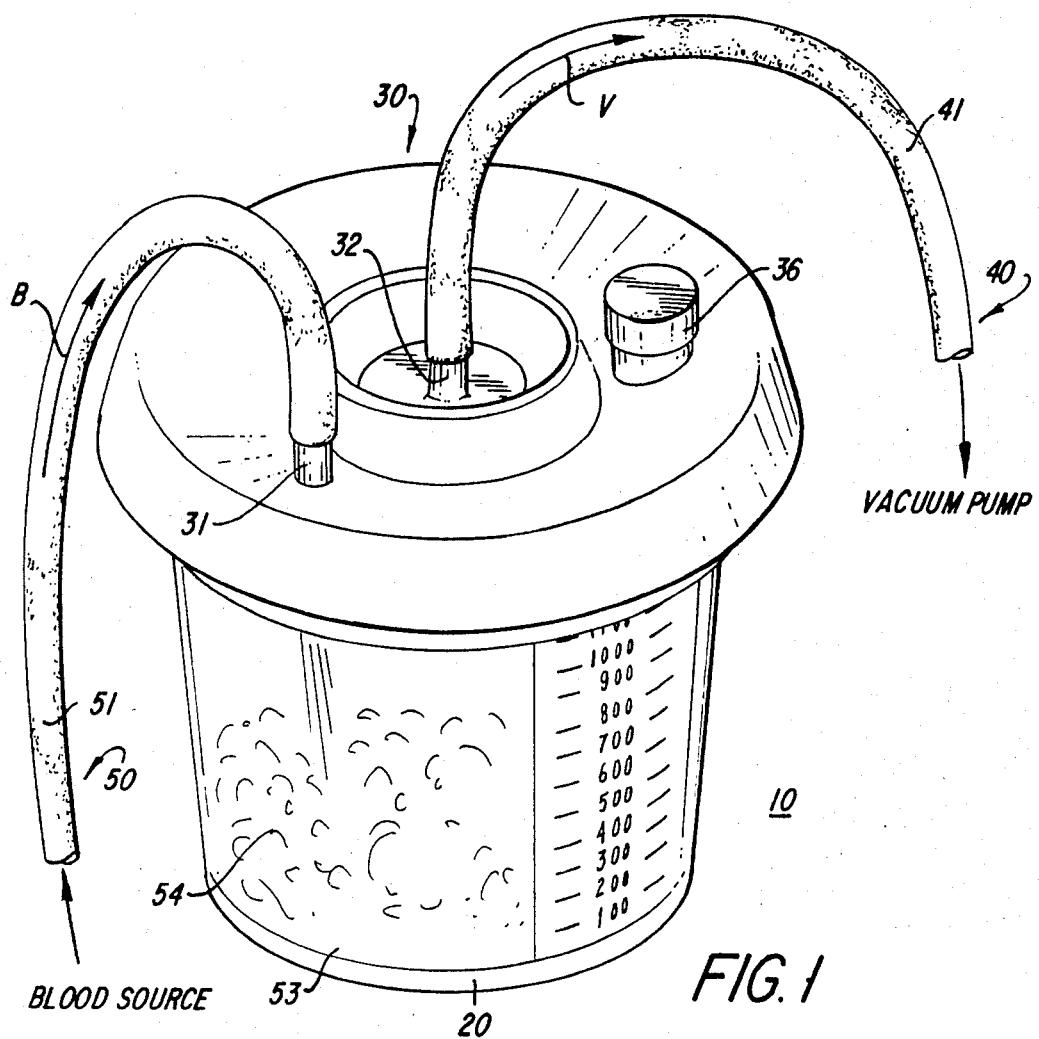
FIG. 1 is a perspective view of a collection system for fluid for use in accordance with the invention.

With reference to the drawings, an illustrative collection system 10 in accordance with the invention is shown in FIG. 1.

The collection system 10 includes a disposable container or cannister 20 which is closed at its top by a removable closure or lid 30. The latter includes an inlet port 31 for fluid being collected. Illustratively, in FIG.

1, the fluid is blood which is drawn from the arm of a patient by a line 50. Suction for drawing the blood over the line 50 is provided by a vacuum arrangement 40 which makes use of a vacuum pump (not shown) connected to a line 41 that extends to the suction inlet 32 in the top of the closure 30.

When the pump of the vacuum system is operated, blood is sucked into the line 51 forming a liquid 53 in the base of the container 20. In addition the suction provides a froth 54 which gives rise to an aerosol that can enter the suction system and result in contamination which is substantially eliminated by the controller arrangement 60 shown in FIG. 2. In a typical application, the pump is 1/20th of a horsepower, providing between 0 inches and 20 inches of mercury (up to 50.8 centimeters).

The closure 30 of the system 10 in FIG. 1 also includes a pouring spout 36 which is covered by a cap 36c. In a typical application, the fluid collected in the vessel 20 is poured from it by removal of the cap 36c and using the pouring spout 36, following which the fitting 40 and 50 are removed and the container 20 and the closure 30 are discarded as a unit.

Figure 2:
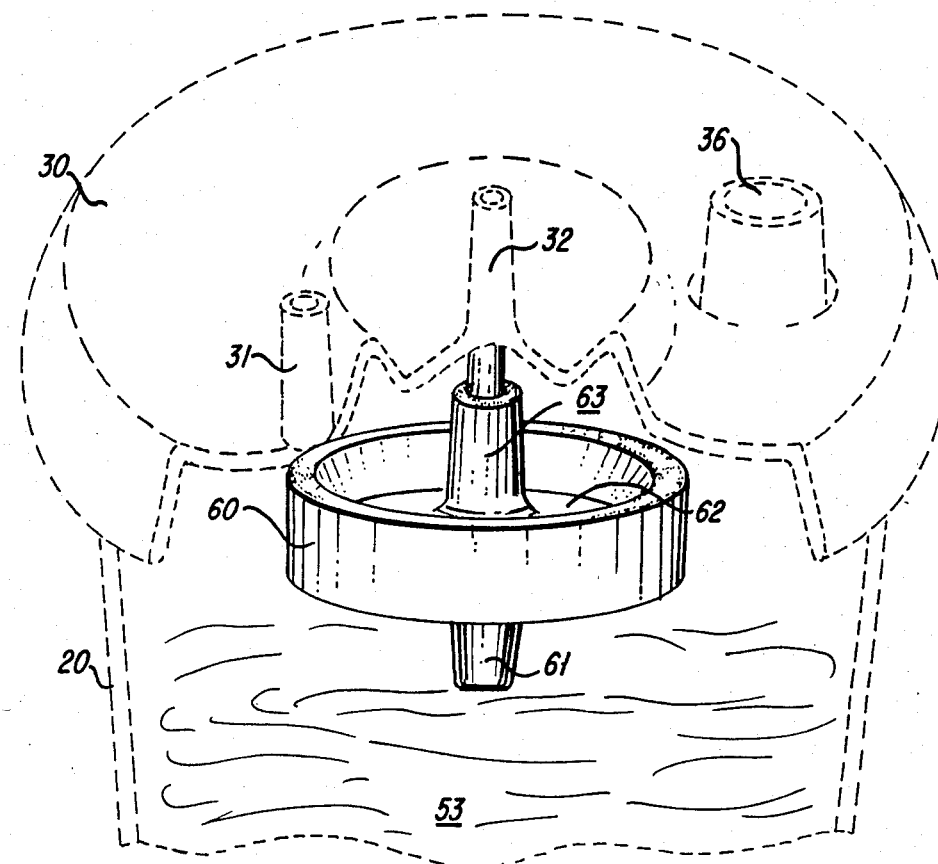
FIG. 2 is a cross-sectional view of the closure for the collection container of FIG. 1 showing a cut-off level control chamber in accordance with the invention.

The controller arrangement 60 that protects the suctional system in the closure lid 30 is shown in section in FIG. 2. The arrangement 60 includes an inlet 61, a oblate spheroidal filter chamber 62 and a filter outlet 63, which is removably connectable to the extension 33 of the suctional inlet 32.

Figure 3A:
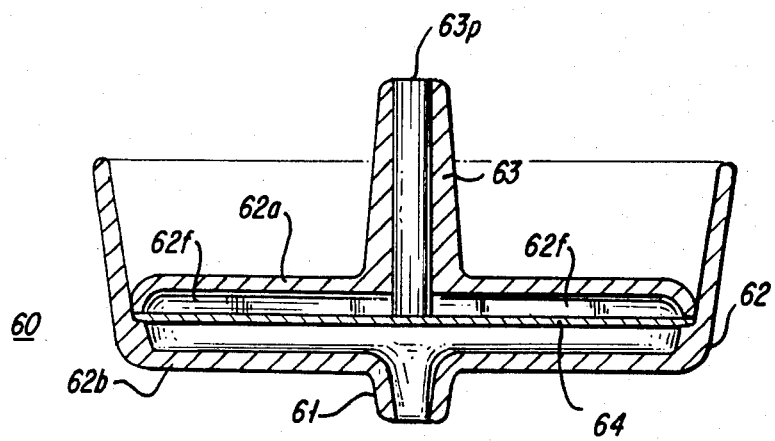
FIG. 3A is a cross-sectional view of the cut-off level control chamber of FIG. 2.

The cut-off controller 60, shown in section in FIG. 3A is in the form of a oblate spheriod with a cup 62b and a cover 62a with a filter element 64. At the mouth of the openng 63p are diagonal fins 62f. The fins 62f lie along the radial line that extends to the center of the cylindrical cover 62a.

Figure 3B:
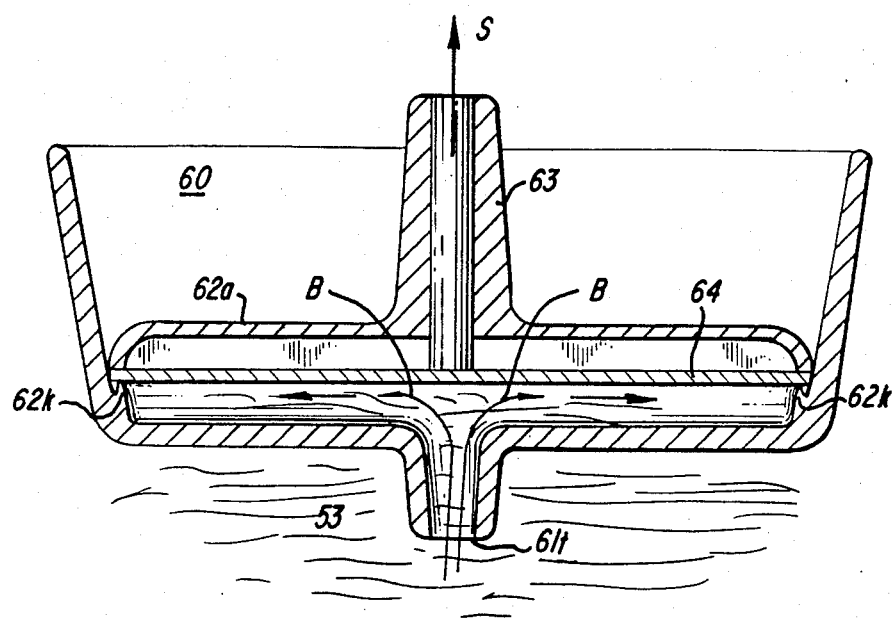
FIG. 3B is a cross-sectional view illustrating the operation of the control chamber of FIG. 3A.

The operation of the controller 60 is illustrated in FIG. 3B. When the level of fluidic material in the container 20 reaches the inlet tube 61t of the base cup 62b, the suctional effect illustrated by the arrow S draws the fluid 53 into the cup 62b as indicated by the arrows B against the filter 64. Since the filter 64 is semi-permeable, allowing only air to pass, the fluid in the cup 62b against the filter 64 produces a blockage and terminates the flow into the outlet 63.

Figure 4A:
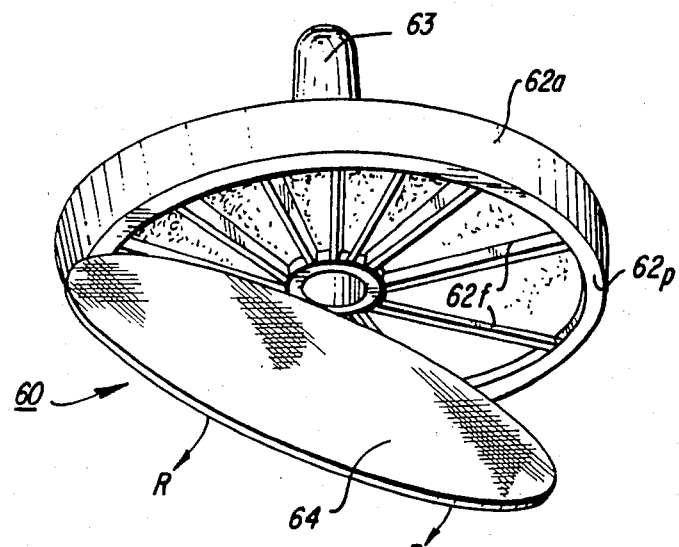
FIG. 4A is a perspective view of the upper portion of the control chamber and the associated filter element.

The rib construction for the fins 62f is illustrated in the partial perspective view of FIG. 4A. Also illustrated in FIG. 4A is the filter element 64 shown separated from the closure 62a in the direction of the arrows R. To promote the cut-off action of the controller 60, the filter element 64 is seated against the lip 62p to form an air tight seal. This seal is promoted by the presence of a peripheral knife edge 62k the cup 62b as shown in FIG. 3B.

Figure 4B:
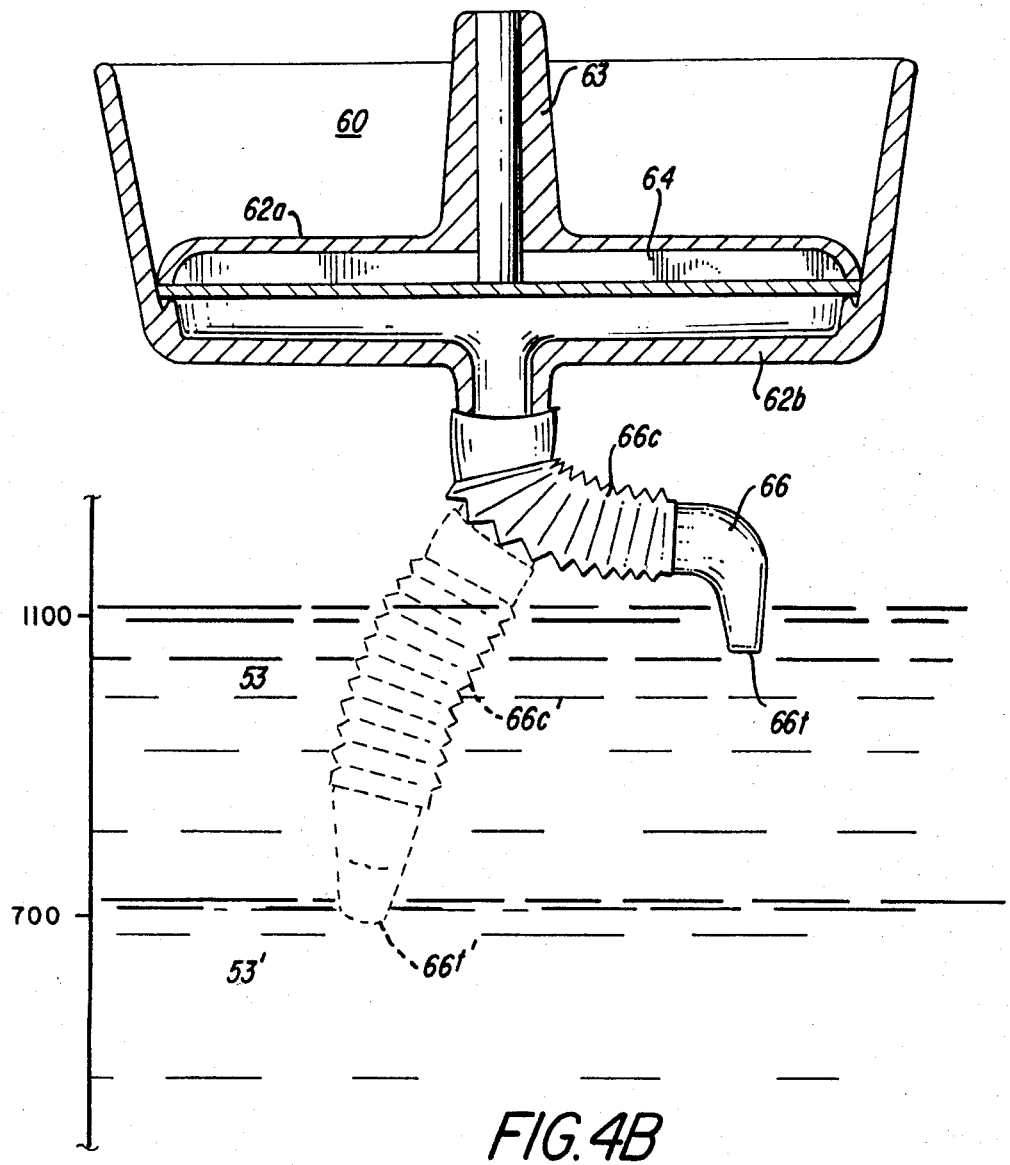
FIG. 4B is a side view of the control chamber with a positionable inlet.

In addition, in order to accurately control the level at which the desired cut-off takes place, the controller 60 can be provided with a flexible inlet extension 66 as shown in FIG. 4B. The extension 66 is positionable on the inlet 61 as a press fit, for example. Its body portion includes corrugations 66c which allow the extension 66 to be adjusted and permit the tip 66t to assume various filler levels, for example 1100 units, and, as illustrated in phantom 700 units for the tip 66t'.

It will be appreciated that where precise control over the cut-off level is desired, the inlet 61 and the extension 66 can be provided with a capilliary opening which quickly draws fluid into the lower portion of the chamber 62b and provides the desired cut-off of flow.

The filter element 64 is of any appropriate semi-permeable type, for example, hydrophobic filter type FA, catalog No. FALP04700, with a pore size of 1.0 $\mu M$, manufactured by the Millipore Corporation of Bedford, Mass. 01730. Such a filter is disclosed in U.S. Pat. No. 4,063,698. In any case, the filter element 64 is joined to form a hermetic seal with the cover 62a, for example by ultrasonic welding.

While various aspects of the invention have been set forth by the drawings and specification, it is to be understood that the foregoing detailed description is for illustration only and that various changes in parts, as well as the substitution of equivalent constitutents for those shown and described may be made without departing from the spirit and scope of the invention as set forth in the appended claims.

What is claimed is:

1. A closure for a collection container comprising an inlet for fluidic material to be collected in the container; means for applying suction to said closure;
a suctional inlet means suspended from said closure and extending downwardly to the cut-off level of the fluidic material to be collected; and
a filter chamber containing a semi-permeable filter element interposed in said inlet between the opening thereof and said closure;
said suctional inlet means being positionable by an adjustable corrugated extension at different cut-off levels.

2. A closure in accordance with claim 1 wherein said suctional inlet and said filter chamber containing said semipermeable filter are removable from said closure.

3. A closure in accordance with claim 2 wherein said filter chamber has a diameter greater than that of said inlet.

4. A closure in accordance with claim 3 wherein said filter chamber has a compartment below said filter element which becomes filled with fluid when the fluid collected in said container reaches said cut-off level.

5. A closure in accordance with claim 4 wherein said fluid collection compartment has apolished knife edge which is engaged by said filter element to provide a seal relative to the said suction applying means.

6. A closure in accordance with claim 3 wherein said inlet of said filter chamber comprises a suctional tube.

7. A closure in accordance with claim 5 wherein said filter chamber has a compartment above said filter element containing ribs which extend radially from the outlet opening therof.

8. A closure in accordance with claim 1 wherein said filter element is hydrophobic.

9. A closure in accordance with claim 1 wherein said filter element is air-pervious-liquid impervious.

* * * * *